US010619177B2

(12) United States Patent
Lynglev

(10) Patent No.: US 10,619,177 B2
(45) Date of Patent: Apr. 14, 2020

(54) METHOD FOR PRODUCING A PROTEIN HYDROLYSATE

(71) Applicant: Novozymes A/S, Bagsvaerd (DK)

(72) Inventor: Gitte Budolfsen Lynglev, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 179 days.

(21) Appl. No.: 15/531,944

(22) PCT Filed: Dec. 1, 2015

(86) PCT No.: PCT/EP2015/078177
§ 371 (c)(1),
(2) Date: May 31, 2017

(87) PCT Pub. No.: WO2016/087427
PCT Pub. Date: Jun. 9, 2016

(65) Prior Publication Data
US 2019/0032102 A1    Jan. 31, 2019

(30) Foreign Application Priority Data
Dec. 1, 2014 (EP) ..................................... 14195682

(51) Int. Cl.
*C12P 21/06* (2006.01)
*A23J 3/34* (2006.01)

(52) U.S. Cl.
CPC ............... *C12P 21/06* (2013.01); *A23J 3/343* (2013.01); *A23J 3/346* (2013.01); *C12Y 304/11* (2013.01); *C12Y 304/22* (2013.01)

(58) Field of Classification Search
CPC .. C12P 21/06; C12P 7/06; C12P 19/02; C12P 19/14; C12P 7/10; C12P 7/14; C12P 21/02; C12Q 1/37; C12Q 1/6872; C12Q 2521/301; C12Q 2521/319; C12Q 1/34; A61K 2035/115; A61K 31/7004; A61K 31/7016; A61K 31/715; A61K 35/39; A61K 35/74; A61K 35/741; A61K 35/742; A61K 35/744; A61K 35/745; A61K 35/747; A61K 38/46; A61K 9/0031; A61K 9/0053; A61K 9/19; A61K 38/482; A61K 38/4826; A61K 38/486; A61K 38/4873; A61K 38/488; A61K 8/64; A61K 38/00; Y02A 50/401; Y02A 50/414; Y02A 50/473; A23J 3/346; A23J 3/343; A23J 3/344; A23J 3/16; A23J 3/34; A23J 3/08; A23J 3/341; A61Q 19/00; A23K 10/14; A23K 20/147; A23K 50/30; A23K 50/75; A23K 20/142; A23K 20/189; C12H 1/003; C11D 3/386; G16B 20/00; G16B 30/00; H01J 49/00; H01J 49/0418; C12N 9/48; C12N 9/62; C12N 9/82; C12N 9/2402; C12N 9/2417; C12N 9/242; C12N 9/2428; C12N 9/2434; C12N 9/2437; C12N 9/50; C12N 9/58; C12N 15/80; C12N 15/815; C12N 15/1034; C12N 15/62; C12N 9/6424; C12N 9/6472; C12N 9/6478; C12N 9/6489; C12N 9/52; C12N 15/1044; C12N 9/485; C12N 9/6427; C12N 9/64; A23L 27/21; A23L 27/24; A23L 27/22; A23L 5/25; A23L 2/02; A23L 2/84; A23L 33/18; A23L 33/40; A23V 2002/00; A23V 2300/06; A21D 8/042; A21D 2/267; A21D 2/268; A21D 2/265; C12Y 304/11001; C12Y 304/11004; C12Y 304/15001; C12Y 304/15005; C12Y 304/16002; C12Y 304/16005; C12Y 304/16006; C12Y 304/17001; C12Y 304/17002; C12Y 304/17003; C12Y 304/17004; C12Y 304/17006; C12Y 304/17011; C12Y 304/21004; C12Y 304/21019; C12Y 304/21026; C12Y 304/2105; C12Y 304/21057; C12Y 304/22025; C12Y 304/24033; C12Y 305/01001; C12Y 305/01043; C12Y 305/01044; C12Y 302/01001; C12Y 302/01003; C12Y 302/01004; C12Y 302/01028; C12Y 304/11; C12Y 304/22; C12Y 304/14; C12Y 304/1409; Y02E 50/17; Y02E 50/16; C07H 21/04; C13K 1/06; C13K 2319/00; C13K 14/001; C13K 14/415; C13K 2299/00; C07K 14/003; C07K 1/128; C07K 2319/00; C07K 14/001; C07K 14/415; C07K 2299/00; G01N 33/6848; G01N 2333/38; G01N 33/56961; G01N 33/573;
(Continued)

(56) References Cited

U.S. PATENT DOCUMENTS 5,705,379 A    1/1998 Wilson
6,465,209 B1* 10/2002 Blinkovsky ............ A21D 2/267
                                                    435/68.1

FOREIGN PATENT DOCUMENTS

EP    0870833 A1   10/1998
WO    1993/08702 A1  5/1993
(Continued)

OTHER PUBLICATIONS

Blaz et al, 2004, Acta Chim Slov, vol. 51, pp. 177-188.
(Continued)

*Primary Examiner* — Deborah K Ware
(74) *Attorney, Agent, or Firm* — Elias Lambiris

(57) ABSTRACT

The present invention relates to a method of producing a protein hydrolysate comprising a step of enzymatic protein hydrolysis performed at high temperature.

20 Claims, No Drawings
Specification includes a Sequence Listing.

(58) Field of Classification Search
CPC .......... G01N 33/6845; G01N 2500/00; G01N 33/6818; G01N 33/6842; G01N 33/6851; A23C 19/05; A23C 19/054; A23C 3/02; A23C 19/0328; A23C 19/043; A23C 19/053; A23C 19/0684
See application file for complete search history.

(56) References Cited

FOREIGN PATENT DOCUMENTS

| | | |
|---|---|---|
| WO | 1994/25580 A1 | 10/1994 |
| WO | 2009/147105 A2 | 12/2009 |
| WO | 2010/078462 A1 | 7/2010 |

OTHER PUBLICATIONS

Ordonez et al, 2008, Bioresource Tech, vol. 99, No. 11, pp. 4749-4754.
Villanueva et al, 1999, Grasas Y Aceites, vol. 50, No. 6, pp. 472-476.
Byun et al., J. Agric. Food Chem., vol. 49, pp. 2061-2063 (2001).

\* cited by examiner

SEQUENCE LISTING

<160> NUMBER OF SEQ ID NOS: 8

<210> SEQ ID NO 1
<211> LENGTH: 1572
<212> TYPE: DNA
<213> ORGANISM: Pyrococcus furiosus
<220> FEATURE:
<221> NAME/KEY: CDS
<222> LOCATION: (1)..(1572)

<400> SEQUENCE: 1

```
atg gca cct gag aag aaa gtt gag caa gtt cgc aac gta gag aaa aac    48
Met Ala Pro Glu Lys Lys Val Glu Gln Val Arg Asn Val Glu Lys Asn
1               5                   10                  15 tac ggt ctt ctt aca cca ggc ctt ttc cgc aaa atc caa aaa ctt aac    96
Tyr Gly Leu Leu Thr Pro Gly Leu Phe Arg Lys Ile Gln Lys Leu Asn
            20                  25                  30 cct aac gag gag atc agc act gta atc gtt ttt gag aac cat cgc gag    144
Pro Asn Glu Glu Ile Ser Thr Val Ile Val Phe Glu Asn His Arg Glu
        35                  40                  45 aag gag atc gct gtt cgc gtt ctt gag ctt atg ggt gcg aag gta cgc    192
Lys Glu Ile Ala Val Arg Val Leu Glu Leu Met Gly Ala Lys Val Arg
    50                  55                  60 tac gtt tac cat atc att ccg gct att gcg gct gac ctt aag gtt cgc    240
Tyr Val Tyr His Ile Ile Pro Ala Ile Ala Ala Asp Leu Lys Val Arg
65                  70                  75                  80 gac ctt ctt gtt atc tct ggt ctt act ggt ggc aaa gcg aaa ctt tca    288
Asp Leu Leu Val Ile Ser Gly Leu Thr Gly Gly Lys Ala Lys Leu Ser
                85                  90                  95 ggc gtt cgc ttc atc caa gag gac tac aaa gtt act gta tct gct gag    336
Gly Val Arg Phe Ile Gln Glu Asp Tyr Lys Val Thr Val Ser Ala Glu
            100                 105                 110 ctt gag gga ctt gac gag tca gcg gca caa gta atg gca aca tac gta    384
Leu Glu Gly Leu Asp Glu Ser Ala Ala Gln Val Met Ala Thr Tyr Val
        115                 120                 125 tgg aac ctt ggc tac gac ggt tct ggc atc act atc ggc atc atc gac    432
Trp Asn Leu Gly Tyr Asp Gly Ser Gly Ile Thr Ile Gly Ile Ile Asp
    130                 135                 140 acg ggc atc gac gct tca cac cct gac ctt caa ggt aag gta atc ggt    480
Thr Gly Ile Asp Ala Ser His Pro Asp Leu Gln Gly Lys Val Ile Gly
145                 150                 155                 160 tgg gtt gac ttc gtt aat ggt cgc tct tat ccg tat gac gac cat ggc    528
Trp Val Asp Phe Val Asn Gly Arg Ser Tyr Pro Tyr Asp Asp His Gly
                165                 170                 175 cac ggt aca cac gta gca tct atc gca gct ggc act ggc gca gct tct    576
His Gly Thr His Val Ala Ser Ile Ala Ala Gly Thr Gly Ala Ala Ser
            180                 185                 190 aac ggc aag tac aaa ggc atg gca cct ggt gcg aaa ctt gct ggt atc    624
Asn Gly Lys Tyr Lys Gly Met Ala Pro Gly Ala Lys Leu Ala Gly Ile
        195                 200                 205 aaa gta ctt ggc gca gac ggt tct ggc tca atc agc aca atc atc aaa    672
Lys Val Leu Gly Ala Asp Gly Ser Gly Ser Ile Ser Thr Ile Ile Lys
    210                 215                 220 ggc gtt gag tgg gct gtt gac aac aag gac aaa tac ggt atc aaa gtt    720
Gly Val Glu Trp Ala Val Asp Asn Lys Asp Lys Tyr Gly Ile Lys Val
225                 230                 235                 240
```

```
atc aac ctt tct ctt ggc tct tct caa agc tct gac ggc aca gac gcg    768
Ile Asn Leu Ser Leu Gly Ser Ser Gln Ser Ser Asp Gly Thr Asp Ala
        245                 250                 255 ctt tca caa gct gtt aac gct gct tgg gac gct ggt ctt gta gtt gtt    816
Leu Ser Gln Ala Val Asn Ala Ala Trp Asp Ala Gly Leu Val Val Val
        260                 265                 270 gtt gct gct ggt aac agc ggt cca aac aaa tac act atc ggc tca ccg    864
Val Ala Ala Gly Asn Ser Gly Pro Asn Lys Tyr Thr Ile Gly Ser Pro
    275                 280                 285 gca gct gcg tct aaa gta atc aca gtt gga gct gta gac aaa tac gac    912
Ala Ala Ala Ser Lys Val Ile Thr Val Gly Ala Val Asp Lys Tyr Asp
290                 295                 300 gtt atc act tct ttc tca tct cgt ggc cct act gca gat ggt cgc ctt    960
Val Ile Thr Ser Phe Ser Ser Arg Gly Pro Thr Ala Asp Gly Arg Leu
305                 310                 315                 320 aaa cca gag gtt gta gca cca ggc aac tgg atc atc gca gct cgc gct   1008
Lys Pro Glu Val Val Ala Pro Gly Asn Trp Ile Ile Ala Ala Arg Ala
                325                 330                 335 tct ggc aca tca atg ggc caa cca atc aac gac tac tat act gct gcg   1056
Ser Gly Thr Ser Met Gly Gln Pro Ile Asn Asp Tyr Tyr Thr Ala Ala
        340                 345                 350 cca gga act tct atg gct act cca cac gta gca ggt atc gct gca ctt   1104
Pro Gly Thr Ser Met Ala Thr Pro His Val Ala Gly Ile Ala Ala Leu
        355                 360                 365 ctt ctt caa gct cac cct tct tgg acg cct gac aaa gta aag act gca   1152
Leu Leu Gln Ala His Pro Ser Trp Thr Pro Asp Lys Val Lys Thr Ala
    370                 375                 380 ctt atc gag act gct gac atc gtt aaa cct gac gag atc gca gac atc   1200
Leu Ile Glu Thr Ala Asp Ile Val Lys Pro Asp Glu Ile Ala Asp Ile
385                 390                 395                 400 gct tat ggt gct ggt cgc gtt aat gcg tac aag gct atc aac tat gac   1248
Ala Tyr Gly Ala Gly Arg Val Asn Ala Tyr Lys Ala Ile Asn Tyr Asp
                405                 410                 415 aac tat gct aaa ctt gta ttc acg ggc tac gta gct aac aaa ggc tct   1296
Asn Tyr Ala Lys Leu Val Phe Thr Gly Tyr Val Ala Asn Lys Gly Ser
        420                 425                 430 caa acg cac caa ttt gtt atc tct ggc gca agc ttc gtt act gct act   1344
Gln Thr His Gln Phe Val Ile Ser Gly Ala Ser Phe Val Thr Ala Thr
        435                 440                 445 ctt tac tgg gac aac gct aac tct gac ctt gac ctt tac tta tac gac   1392
Leu Tyr Trp Asp Asn Ala Asn Ser Asp Leu Asp Leu Tyr Leu Tyr Asp
    450                 455                 460 cca aac ggc aac cag gtt gac tat tct tat act gca tac tac gac ttt   1440
Pro Asn Gly Asn Gln Val Asp Tyr Ser Tyr Thr Ala Tyr Tyr Asp Phe
465                 470                 475                 480 gag aag gtt ggc tat tac aac cct act gac ggc aca tgg aca atc aaa   1488
Glu Lys Val Gly Tyr Tyr Asn Pro Thr Asp Gly Thr Trp Thr Ile Lys
                485                 490                 495 gta gta agc tat tca gga tca gct aac tac caa gta gac gta gtt tct   1536
Val Val Ser Tyr Ser Gly Ser Ala Asn Tyr Gln Val Asp Val Val Ser
            500                 505                 510 gac ggt tct ctt agc cag cct ggc tca tca cca taa                   1572
Asp Gly Ser Leu Ser Gln Pro Gly Ser Ser Pro
        515                 520
```

<210> SEQ ID NO 2
<211> LENGTH: 523
<212> TYPE: PRT
<213> ORGANISM: Pyrococcus furiosus

<400> SEQUENCE: 2

```
Met Ala Pro Glu Lys Lys Val Glu Gln Val Arg Asn Val Lys Asn
1               5                   10                  15

Tyr Gly Leu Leu Thr Pro Gly Leu Phe Arg Lys Ile Gln Lys Leu Asn
            20                  25                  30

Pro Asn Glu Glu Ile Ser Thr Val Ile Val Phe Glu Asn His Arg Glu
            35                  40                  45

Lys Glu Ile Ala Val Arg Val Leu Glu Leu Met Gly Ala Lys Val Arg
        50                  55                  60

Tyr Val Tyr His Ile Ile Pro Ala Ile Ala Ala Asp Leu Lys Val Arg
65                  70                  75                  80

Asp Leu Leu Val Ile Ser Gly Leu Thr Gly Gly Lys Ala Lys Leu Ser
                85                  90                  95

Gly Val Arg Phe Ile Gln Glu Asp Tyr Lys Val Thr Val Ser Ala Glu
                100                 105                 110

Leu Glu Gly Leu Asp Glu Ser Ala Ala Gln Val Met Ala Thr Tyr Val
            115                 120                 125

Trp Asn Leu Gly Tyr Asp Gly Ser Gly Ile Thr Ile Gly Ile Ile Asp
130                 135                 140

Thr Gly Ile Asp Ala Ser His Pro Asp Leu Gln Gly Lys Val Ile Gly
145                 150                 155                 160

Trp Val Asp Phe Val Asn Gly Arg Ser Tyr Pro Tyr Asp Asp His Gly
                165                 170                 175

His Gly Thr His Val Ala Ser Ile Ala Ala Gly Thr Gly Ala Ala Ser
            180                 185                 190

Asn Gly Lys Tyr Lys Gly Met Ala Pro Gly Ala Lys Leu Ala Gly Ile
        195                 200                 205

Lys Val Leu Gly Ala Asp Gly Ser Gly Ser Ile Ser Thr Ile Ile Lys
210                 215                 220

Gly Val Glu Trp Ala Val Asp Asn Lys Asp Lys Tyr Gly Ile Lys Val
225                 230                 235                 240

Ile Asn Leu Ser Leu Gly Ser Ser Gln Ser Ser Asp Gly Thr Asp Ala
                245                 250                 255

Leu Ser Gln Ala Val Asn Ala Ala Trp Asp Ala Gly Leu Val Val Val
            260                 265                 270

Val Ala Ala Gly Asn Ser Gly Pro Asn Lys Tyr Thr Ile Gly Ser Pro
        275                 280                 285

Ala Ala Ala Ser Lys Val Ile Thr Val Gly Ala Val Asp Lys Tyr Asp
290                 295                 300

Val Ile Thr Ser Phe Ser Ser Arg Gly Pro Thr Ala Asp Gly Arg Leu
305                 310                 315                 320

Lys Pro Glu Val Val Ala Pro Gly Asn Trp Ile Ile Ala Ala Arg Ala
                325                 330                 335

Ser Gly Thr Ser Met Gly Gln Pro Ile Asn Asp Tyr Tyr Thr Ala Ala
            340                 345                 350

Pro Gly Thr Ser Met Ala Thr Pro His Val Ala Gly Ile Ala Ala Leu
        355                 360                 365

Leu Leu Gln Ala His Pro Ser Trp Thr Pro Asp Lys Val Lys Thr Ala
370                 375                 380

Leu Ile Glu Thr Ala Asp Ile Val Lys Pro Asp Glu Ile Ala Asp Ile
385                 390                 395                 400

Ala Tyr Gly Ala Gly Arg Val Asn Ala Tyr Lys Ala Ile Asn Tyr Asp
                405                 410                 415
```

```
Asn Tyr Ala Lys Leu Val Phe Thr Gly Tyr Val Ala Asn Lys Gly Ser
                420                 425                 430

Gln Thr His Gln Phe Val Ile Ser Gly Ala Ser Phe Val Thr Ala Thr
            435                 440                 445

Leu Tyr Trp Asp Asn Ala Asn Ser Asp Leu Asp Leu Tyr Leu Tyr Asp
        450                 455                 460

Pro Asn Gly Asn Gln Val Asp Tyr Ser Tyr Thr Ala Tyr Tyr Asp Phe
465                 470                 475                 480

Glu Lys Val Gly Tyr Tyr Asn Pro Thr Asp Gly Thr Trp Thr Ile Lys
                485                 490                 495

Val Val Ser Tyr Ser Gly Ser Ala Asn Tyr Gln Val Asp Val Val Ser
            500                 505                 510

Asp Gly Ser Leu Ser Gln Pro Gly Ser Pro
            515                 520

<210> SEQ ID NO 3
<211> LENGTH: 413
<212> TYPE: PRT
<213> ORGANISM: Pyrococcus furiosus

<400> SEQUENCE: 3

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
```

```
                    260                 265                 270
Thr Ala Leu Ile Glu Thr Ala Asp Ile Val Lys Pro Asp Glu Ile Ala
                275                 280                 285

Asp Ile Ala Tyr Gly Ala Gly Arg Val Asn Ala Tyr Lys Ala Ile Asn
            290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
                355                 360                 365

Asp Phe Glu Lys Val Gly Tyr Tyr Asn Pro Thr Asp Gly Thr Trp Thr
            370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 4
<211> LENGTH: 188
<212> TYPE: PRT
<213> ORGANISM: Nocardiopsis sp.

<400> SEQUENCE: 4

Ala Asp Ile Ile Gly Gly Leu Ala Tyr Thr Met Gly Gly Arg Cys Ser
1               5                  10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 5
<211> LENGTH: 1107
<212> TYPE: DNA
<213> ORGANISM: Thermobifida fusca
<220> FEATURE:
```

<221> NAME/KEY: CDS
<222> LOCATION: (1)..(1107)

<400> SEQUENCE: 5

```
gtg aac cat tcc tcc cga aga acc acc tcc ctc ctt ttc act gcc gcg       48
Val Asn His Ser Ser Arg Arg Thr Thr Ser Leu Leu Phe Thr Ala Ala
1               5                   10                  15 ctg gcc gcc act gca ctg gtc gcc gcc acc acc ccc gcc tcc gcc caa       96
Leu Ala Ala Thr Ala Leu Val Ala Ala Thr Thr Pro Ala Ser Ala Gln
            20                  25                  30 gag ctc gcc ctc aaa cgc gac ctc ggg ttg agc gac gct gaa gtc gcg      144
Glu Leu Ala Leu Lys Arg Asp Leu Gly Leu Ser Asp Ala Glu Val Ala
        35                  40                  45 gaa ctg cgc gcc gcc gaa gcc gaa gca gtc gag ctg gaa gag gag ctg      192
Glu Leu Arg Ala Ala Glu Ala Glu Ala Val Glu Leu Glu Glu Glu Leu
    50                  55                  60 cgc gac tcc ctc ggc tcc gat ttc ggc ggc gtc tac ttg gac gcg gac      240
Arg Asp Ser Leu Gly Ser Asp Phe Gly Gly Val Tyr Leu Asp Ala Asp
65                  70                  75                  80 acc aca gag atc acg gtc gcc gtc acc gac ccc gcc gcc gtg tcc cgt      288
Thr Thr Glu Ile Thr Val Ala Val Thr Asp Pro Ala Ala Val Ser Arg
                85                  90                  95 gtc gac gcg gac gac gtc acc gtg gac gtt gtt gat ttc ggg gaa acc      336
Val Asp Ala Asp Asp Val Thr Val Asp Val Val Asp Phe Gly Glu Thr
            100                 105                 110 gcc ctc aac gac ttc gtg gcg tcc ctc aac gcg atc gct gac acc gct      384
Ala Leu Asn Asp Phe Val Ala Ser Leu Asn Ala Ile Ala Asp Thr Ala
        115                 120                 125 gac cca aag gtc acc ggc tgg tac acc gac ctg gag tcc gat gcg gta      432
Asp Pro Lys Val Thr Gly Trp Tyr Thr Asp Leu Glu Ser Asp Ala Val
    130                 135                 140 gtc atc acc acg ctc cgg ggc ggc act ccg gca gcc gaa gag ctc gcc      480
Val Ile Thr Thr Leu Arg Gly Gly Thr Pro Ala Ala Glu Glu Leu Ala
145                 150                 155                 160 gag cgg gct ggt ctg gac gag cgg gcc gtg cgc att gtc gaa gag gac      528
Glu Arg Ala Gly Leu Asp Glu Arg Ala Val Arg Ile Val Glu Glu Asp
                165                 170                 175 gaa gag ccg cag tcc ctt gcc gcc atc atc ggc ggc aac ccc tac tat      576
Glu Glu Pro Gln Ser Leu Ala Ala Ile Ile Gly Gly Asn Pro Tyr Tyr
            180                 185                 190 ttc ggg aac tac cgc tgc tct atc gga ttc tcg gtc cgc cag ggc agc      624
Phe Gly Asn Tyr Arg Cys Ser Ile Gly Phe Ser Val Arg Gln Gly Ser
        195                 200                 205 cag acc ggc ttc gcc acc gcg ggc cac tgc ggt tcg aca ggc acg cga      672
Gln Thr Gly Phe Ala Thr Ala Gly His Cys Gly Ser Thr Gly Thr Arg
    210                 215                 220 gtc agc tcc ccc tca ggc act gtc gcc gga tcg tac ttc ccc ggc cgt      720
Val Ser Ser Pro Ser Gly Thr Val Ala Gly Ser Tyr Phe Pro Gly Arg
225                 230                 235                 240 gac atg ggc tgg gtg cgt atc acc agc gct gac acc gtc acc ccg ctc      768
Asp Met Gly Trp Val Arg Ile Thr Ser Ala Asp Thr Val Thr Pro Leu
                245                 250                 255 gtc aac cgc tac aac ggc gga acg gtg acc gtc acc ggt tcg cag gag      816
Val Asn Arg Tyr Asn Gly Gly Thr Val Thr Val Thr Gly Ser Gln Glu
            260                 265                 270 gcc gcc acc ggc tct tcg gtg tgc cgc tcc gga gcg acc acc ggg tgg      864
Ala Ala Thr Gly Ser Ser Val Cys Arg Ser Gly Ala Thr Thr Gly Trp
        275                 280                 285 cgc tgc ggc acc atc cag tcg aag aac cag acc gtc cgc tac gcg gaa      912
Arg Cys Gly Thr Ile Gln Ser Lys Asn Gln Thr Val Arg Tyr Ala Glu
    290                 295                 300
```

```
              290                 295                 300
gga  acc  gtc  acc  ggc  ctg  acc  cgc  acc  act  gcc  tgc  gct  gaa  ggc  ggc     960
Gly  Thr  Val  Thr  Gly  Leu  Thr  Arg  Thr  Thr  Ala  Cys  Ala  Glu  Gly  Gly
305                      310                 315                      320 gac  tcc  ggc  ggc  ccg  tgg  ctc  acc  ggt  tcc  caa  gcc  caa  ggg  gtg  acc    1008
Asp  Ser  Gly  Gly  Pro  Trp  Leu  Thr  Gly  Ser  Gln  Ala  Gln  Gly  Val  Thr
               325                      330                      335 tcg  ggc  ggc  acc  ggt  gac  tgc  cgg  tcc  ggc  ggc  atc  acg  ttc  ttc  cag    1056
Ser  Gly  Gly  Thr  Gly  Asp  Cys  Arg  Ser  Gly  Gly  Ile  Thr  Phe  Phe  Gln
               340                      345                      350 ccc  atc  aac  ccg  ctg  ctg  tcc  tac  ttc  gga  ctg  caa  ctg  gtc  acc  ggc    1104
Pro  Ile  Asn  Pro  Leu  Leu  Ser  Tyr  Phe  Gly  Leu  Gln  Leu  Val  Thr  Gly
               355                      360                 365 tga                                                                                1107
```

<210> SEQ ID NO 6
<211> LENGTH: 368
<212> TYPE: PRT
<213> ORGANISM: Thermobifida fusca

<400> SEQUENCE: 6

```
Met  Asn  His  Ser  Ser  Arg  Arg  Thr  Thr  Ser  Leu  Leu  Phe  Thr  Ala  Ala
1                  5                       10                      15

Leu  Ala  Thr  Ala  Leu  Val  Ala  Ala  Thr  Thr  Pro  Ala  Ser  Ala  Gln
          20                      25                      30

Glu  Leu  Ala  Leu  Lys  Arg  Asp  Leu  Gly  Leu  Ser  Asp  Ala  Glu  Val  Ala
               35                      40                      45

Glu  Leu  Arg  Ala  Ala  Glu  Ala  Val  Glu  Leu  Glu  Glu  Leu
50                      55                      60

Arg  Asp  Ser  Leu  Gly  Ser  Asp  Phe  Gly  Gly  Val  Tyr  Leu  Asp  Ala  Asp
65                      70                      75                      80

Thr  Thr  Glu  Ile  Thr  Val  Ala  Val  Thr  Asp  Pro  Ala  Ala  Val  Ser  Arg
                    85                      90                      95

Val  Asp  Ala  Asp  Asp  Val  Thr  Val  Asp  Val  Val  Asp  Phe  Gly  Glu  Thr
               100                     105                     110

Ala  Leu  Asn  Asp  Phe  Val  Ala  Ser  Leu  Asn  Ala  Ile  Ala  Asp  Thr  Ala
               115                     120                     125

Asp  Pro  Lys  Val  Thr  Gly  Trp  Tyr  Thr  Asp  Leu  Glu  Ser  Asp  Ala  Val
          130                     135                     140

Val  Ile  Thr  Thr  Leu  Arg  Gly  Gly  Thr  Pro  Ala  Ala  Glu  Glu  Leu  Ala
145                     150                     155                     160

Glu  Arg  Ala  Gly  Leu  Asp  Glu  Arg  Ala  Val  Arg  Ile  Val  Glu  Glu  Asp
                    165                     170                     175

Glu  Glu  Pro  Gln  Ser  Leu  Ala  Ala  Ile  Ile  Gly  Gly  Asn  Pro  Tyr  Tyr
               180                     185                     190

Phe  Gly  Asn  Tyr  Arg  Cys  Ser  Ile  Gly  Phe  Ser  Val  Arg  Gln  Gly  Ser
               195                     200                     205

Gln  Thr  Gly  Phe  Ala  Thr  Ala  Gly  His  Cys  Gly  Ser  Thr  Gly  Thr  Arg
          210                     215                     220

Val  Ser  Ser  Pro  Ser  Gly  Thr  Val  Ala  Gly  Ser  Tyr  Phe  Pro  Gly  Arg
225                     230                     235                     240

Asp  Met  Gly  Trp  Val  Arg  Ile  Thr  Ser  Ala  Asp  Thr  Val  Thr  Pro  Leu
                    245                     250                     255

Val  Asn  Arg  Tyr  Asn  Gly  Gly  Thr  Val  Thr  Val  Thr  Gly  Ser  Gln  Glu
               260                     265                     270
```

```
Ala Ala Thr Gly Ser Ser Val Cys Arg Ser Gly Ala Thr Gly Trp
            275                 280                 285

Arg Cys Gly Thr Ile Gln Ser Lys Asn Gln Thr Val Arg Tyr Ala Glu
            290                 295                 300

Gly Thr Val Thr Gly Leu Thr Arg Thr Ala Cys Ala Glu Gly Gly
305                 310                 315                 320

Asp Ser Gly Gly Pro Trp Leu Thr Gly Ser Gln Ala Gln Val Thr
                325                 330                 335

Ser Gly Gly Thr Gly Asp Cys Arg Ser Gly Gly Ile Thr Phe Phe Gln
            340                 345                 350

Pro Ile Asn Pro Leu Leu Ser Tyr Phe Gly Leu Gln Leu Val Thr Gly
            355                 360                 365
```

<210> SEQ ID NO 7
<211> LENGTH: 371
<212> TYPE: PRT
<213> ORGANISM: Thermobifida fusca

<400> SEQUENCE: 7

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Gln Glu Leu Ala Leu
            20                  25                  30

Lys Arg Asp Leu Gly Leu Ser Asp Ala Glu Val Ala Glu Leu Arg Ala
        35                  40                  45

Ala Glu Ala Glu Ala Val Glu Leu Glu Glu Leu Arg Asp Ser Leu
50                  55                  60

Gly Ser Asp Phe Gly Gly Val Tyr Leu Asp Ala Asp Thr Thr Glu Ile
65                  70                  75                  80

Thr Val Ala Val Thr Asp Pro Ala Ala Val Ser Arg Val Asp Ala Asp
                85                  90                  95

Asp Val Thr Val Asp Val Val Asp Phe Gly Glu Thr Ala Leu Asn Asp
            100                 105                 110

Phe Val Ala Ser Leu Asn Ala Ile Ala Asp Thr Ala Asp Pro Lys Val
        115                 120                 125

Thr Gly Trp Tyr Thr Asp Leu Glu Ser Asp Ala Val Val Ile Thr Thr
130                 135                 140

Leu Arg Gly Gly Thr Pro Ala Ala Glu Glu Leu Ala Glu Arg Ala Gly
145                 150                 155                 160

Leu Asp Glu Arg Ala Val Arg Ile Val Glu Glu Asp Glu Pro Gln
                165                 170                 175

Ser Leu Ala Ala Ile Ile Gly Gly Asn Pro Tyr Tyr Phe Gly Asn Tyr
            180                 185                 190

Arg Cys Ser Ile Gly Phe Ser Val Arg Gln Gly Ser Gln Thr Gly Phe
        195                 200                 205

Ala Thr Ala Gly His Cys Gly Ser Thr Gly Thr Arg Val Ser Ser Pro
    210                 215                 220

Ser Gly Thr Val Ala Gly Ser Tyr Phe Pro Gly Arg Asp Met Gly Trp
225                 230                 235                 240

Val Arg Ile Thr Ser Ala Asp Thr Val Thr Pro Leu Val Asn Arg Tyr
                245                 250                 255

Asn Gly Gly Thr Val Thr Val Thr Gly Ser Gln Glu Ala Ala Thr Gly
            260                 265                 270

Ser Ser Val Cys Arg Ser Gly Ala Thr Thr Gly Trp Arg Cys Gly Thr
        275                 280                 285
```

```
Ile Gln Ser Lys Asn Gln Thr Val Arg Tyr Ala Glu Gly Thr Val Thr
    290                 295                 300

Gly Leu Thr Arg Thr Thr Ala Cys Ala Glu Gly Gly Asp Ser Gly Gly
305                 310                 315                 320

Pro Trp Leu Thr Gly Ser Gln Ala Gln Gly Val Thr Ser Gly Gly Thr
                325                 330                 335

Gly Asp Cys Arg Ser Gly Gly Ile Thr Phe Phe Gln Pro Ile Asn Pro
                340                 345                 350

Leu Leu Ser Tyr Phe Gly Leu Gln Leu Val Thr Gly His Gln His Gln
        355                 360                 365

His Gln His
    370

<210> SEQ ID NO 8
<211> LENGTH: 186
<212> TYPE: PRT
<213> ORGANISM: Thermobifida fusca

<400> SEQUENCE: 8

Ala Ala Ile Ile Gly Gly Asn Pro Tyr Tyr Phe Gly Asn Tyr Arg Cys
1               5                   10                  15

Ser Ile Gly Phe Ser Val Arg Gln Gly Ser Gln Thr Gly Phe Ala Thr
                20                  25                  30

Ala Gly His Cys Gly Ser Thr Gly Thr Arg Val Ser Ser Pro Ser Gly
            35                  40                  45

Thr Val Ala Gly Ser Tyr Phe Pro Gly Arg Asp Met Gly Trp Val Arg
50                  55                  60

Ile Thr Ser Ala Asp Thr Val Thr Pro Leu Val Asn Arg Tyr Asn Gly
65                  70                  75                  80

Gly Thr Val Thr Val Thr Gly Ser Gln Glu Ala Ala Thr Gly Ser Ser
                85                  90                  95

Val Cys Arg Ser Gly Ala Thr Thr Gly Trp Arg Cys Gly Thr Ile Gln
                100                 105                 110

Ser Lys Asn Gln Thr Val Arg Tyr Ala Glu Gly Thr Val Thr Gly Leu
            115                 120                 125

Thr Arg Thr Thr Ala Cys Ala Glu Gly Gly Asp Ser Gly Gly Pro Trp
        130                 135                 140

Leu Thr Gly Ser Gln Ala Gln Gly Val Thr Ser Gly Gly Thr Gly Asp
145                 150                 155                 160

Cys Arg Ser Gly Gly Ile Thr Phe Phe Gln Pro Ile Asn Pro Leu Leu
                165                 170                 175

Ser Tyr Phe Gly Leu Gln Leu Val Thr Gly
            180                 185
```

METHOD FOR PRODUCING A PROTEIN HYDROLYSATE

CROSS-REFERENCE TO RELATED APPLICATIONS

This application is a 35 U.S.C. 371 national application of international application no. PCT/EP2015/078177 filed Dec. 1, 2015 which claims priority or the benefit under 35 U.S.C. 119 of European application no. 14195682.1 filed Dec. 1, 2014, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to enzymatic production of protein hydrolysates.

BACKGROUND OF THE INVENTION

Protein hydrolysates are mixtures of polypeptides, oligopeptides and/or amino acids that are man-ufactured from protein sources using partial or complete hydrolysis. There is a growing interest in protein hydrolysate preparations which have many uses, e.g., in human nutrition, e.g., as ingre-dients in energy drinks, weight-control and sports nutrition products, as a source of nutrition for elderly and underweight patients, and in the flavour industry. The protein could be derived from plants, e.g., soy, wheat or corn, or from animals, e.g., milk, eggs, meat or fish.

Production of protein hydrolysates in the food industry involves enzymatic, acid or alkali protein hydrolysis. Chemical hydrolysis is difficult to control and reduces the nutritional quality of the products. Enzymatic hydrolysis works without destructing amino acids and by avoiding the extreme temperatures and pH levels required for chemical hydrolysis, the nutritional properties of the protein hydrolysates remain largely unaffected.

However, for enzymatically hydrolysed protein, the protein yield and the degree of hydrolysis (DH) obtained are often limited.

A key factor limiting the yield and degree of hydrolysis is the conformation of the substrate protein to be hydrolysed. Not unfolded proteins, e.g. globular proteins, will often be more difficult to degrade than unfolded proteins, as it is more difficult for the proteases to degrade folded proteins. A variety of reagents and conditions can cause denaturation and result in the disruption of the secondary and tertiary structure of the protein. Heat can be used to disrupt hydrogen bonds and non-polar hydrophobic interactions a.o. being responsible for the secondary- and tertiary structure; the heating causes the molecules to vibrate so rapidly and violently that these bonds/interactions are disrupted.

It is common practice to unfold or denature the substrate protein by performing a heat treatment before addition of the proteolytic enzymes; however this is not an optimal method as the unfolding or denaturation often requires a high temperature at which the proteolytic enzymes applied are not stable and/or not at their optimum for activity. Especially the exopeptidases have a low thermostability. Lowering the temperature after unfolding will enable the proteins to re-aggregate in a way which will reduce the efficiency of the proteolytic degradation.

It is an object of the present invention to provide protein hydrolysates having improved properties, such as a high solubility, a high degree of hydrolysis, a high protein yield and/or a pleasant flavour.

SUMMARY OF THE INVENTION

The present invention provides a two-step procedure, where the substrate protein is first degraded by an endopeptidase at a temperature which is sufficiently high to both ensure that the substrate protein is unfolded/denatured and to also prevent the substrate protein from re-aggregating. This hydrolysis is carried out by use of a thermostable endopeptidase. Preferably, the thermostable endopeptidase is non-specific. Being nonspecific enables the endopeptidase to degrade the substrate protein to relatively small peptides with limited ability to re-aggregate.

After this first hydrolysis step performed at high temperature, the temperature is lowered and a second hydrolysis step is performed using a protease preparation having a high aminopeptidase activity. Preferably, the protease preparation also has a high carboxypeptidase activity. Such second hydrolysis step provides a deep hydrolysis of the peptides.

The invention provides a method for producing a protein hydrolysate, comprising:
a) adding to a composition comprising substrate protein a thermostable endopeptidase;
b) performing a first hydrolysis step by incubating the composition of step a) for at least 10 minutes at a temperature of at least 75° C.;
c) adding to the composition of step b) a protease preparation having an aminopeptidase activity of at least 200 LAPU/g; and
d) performing a second hydrolysis step by incubating the composition of step c) for at least 10 minutes at a temperature which is at least 10° C. lower than the temperature used in step b).

The invention also provides a method for producing a protein hydrolysate, comprising:
a) adding to a composition comprising substrate protein a thermostable endopeptidase which (i) has at least 60% sequence identity to the polypeptide of SEQ ID NO: 3, (ii) is encoded by a polynucleotide having at least 60% sequence identity to the mature polypeptide coding sequence of SEQ ID NO: 1, or (iii) is a variant of the polypeptide of SEQ ID NO: 3 comprising a substitution, deletion, and/or insertion at one or more positions; and
b) incubating the composition of step a) for at least 10 minutes at a temperature of at least 75° C.

DETAILED DESCRIPTION OF THE INVENTION

Substrate Protein

The substrate protein to be used in the methods of the present invention may be a soy protein. A variety of soy protein materials may be used. In general, the soy protein material may be derived from whole soybeans in accordance with methods known in the art. The whole soybeans may be standard soybeans (i.e., non genetically modified soybeans), genetically modified soybeans, or combinations thereof. Suitable examples of soy protein material include soy extract, soy milk, soy milk powder, soy curd, soy flour, isolated soy protein, soy protein concentrate, and mixtures thereof.

The soy protein may be a soy protein isolate (also called isolated soy protein or ISP). In general, soy protein isolates have a protein content of at least about 90% soy protein on a moisturefree basis. The soy protein isolate may comprise intact soy proteins or it may comprise partially hydrolyzed soy proteins.

The soy protein may be a soy protein concentrate. In general, soy protein concentrates have a protein content of about 65% to less than about 90% on a moisture-free basis. Alternatively, the soy protein may be a soy protein concentrate blended with a soy protein isolate to substitute for a portion of the soy protein isolate as a source of soy protein material. Typically, if a soy protein concentrate is substituted for a portion of the soy protein isolate, the soy protein concentrate is substituted for up to about 40% of the soy protein isolate by weight, at most, and more preferably is substituted for up to about 30% of the soy protein isolate by weight.

The soy protein may be soy flour. In general, soy flour has a protein content of about 49% to about 65% on a moisture-free basis. The soy flour may be defatted soy flour, partially defatted soy flour, or full fat soy flour. The soy flour may be blended with soy protein isolate or soy protein concentrate.

The substrate protein to be used in a method of the present invention material may be derived from a plant other than soy. By way of non-limiting example, suitable plants include amaranth, arrowroot, barley, buckwheat, canola, cassava, channa (garbanzo), legumes, lentils, lupin, maize, millet, oat, pea, potato, rice, rye, sorghum, sunflower, tapioca, triticale, wheat, and mixtures thereof. Especially preferred plant proteins include barley, canola, lupin, maize, oat, pea, potato, rice, wheat, and combinations thereof. In one embodiment, the plant protein material may be canola meal, canola protein isolate, canola protein concentrate, and combinations thereof. In another embodiment, the plant protein material may be maize or corn protein powder, maize or corn protein concentrate, maize or corn protein isolate, maize or corn germ, maize or corn gluten, maize or corn gluten meal, maize or corn flour, zein protein, and combinations thereof. In still another embodiment, the plant protein material may be barley powder, barley protein concentrate, barley protein isolate, barley meal, barley flour, and combinations thereof. In an alternate embodiment, the plant protein material may be lupin flour, lupin protein isolate, lupin protein concentrate, and combinations thereof. In another alternate embodiment, the plant protein material may be oatmeal, oat flour, oat protein flour, oat protein isolate, oat protein concentrate, and combinations thereof. In yet another embodiment, the plant protein material may be pea flour, pea protein isolate, pea protein concentrate, and combinations thereof. In still another embodiment, the plant protein material may be potato protein powder, potato protein isolate, potato protein concentrate, potato flour, and combinations thereof. In a further embodiment, the plant protein material may be rice flour, rice meal, rice protein powder, rice protein isolate, rice protein concentrate, and combinations thereof. In another alternate embodiment, the plant protein material may be wheat protein powder, wheat gluten, wheat germ, wheat flour, wheat protein isolate, wheat protein concentrate, solubilized wheat proteins, and combinations thereof.

The substrate protein to be used in a method of the present invention material may be derived from an animal source. In one embodiment, the animal protein material may be derived from eggs. Non-limiting examples of suitable egg proteins include powdered egg, dried egg solids, dried egg white protein, liquid egg white protein, egg white protein powder, isolated ovalbumin protein, and combinations thereof. Egg proteins may be derived from the eggs of chicken, duck, goose, quail, or other birds. In an alternate embodiment, the protein material may be derived from a dairy source. Suitable dairy proteins include non-fat dry milk powder, milk protein isolate, milk protein concentrate, acid casein, caseinate (e.g., sodium caseinate, calcium caseinate, and the like), whey protein isolate, whey protein concentrate, and combinations thereof. The milk protein material may be derived from cows, goats, sheep, donkeys, camels, camelids, yaks, water buffalos, etc. In a further embodiment, the protein may be derived from the muscles, organs, connective tissues, or skeletons of land-based or aquatic animals. As an example, the animal protein may be gelatin, which is produced by partial hydrolysis of collagen extracted from the bones, connective tissues, organs, etc, from cattle or other animals.

The substrate protein to be used in a method of the present invention material may be a combination of two or more of the protein materials listed above.

In a preferred embodiment, the substrate protein is selected from soy protein, wheat gluten protein or whey protein. In a more preferred embodiment, the substrate protein is soy protein.

The substrate protein to be used in the methods of the present invention is typically mixed or dispersed in water to form an aqueous composition comprising substrate protein.

The composition comprising substrate protein may have a dry matter content of at least 1% (w/w), preferably at least 5% (w/w), more preferably at least 8% (w/w). The composition comprising substrate protein may have a dry matter content of 1-75% (w/w), preferably 5-40% (w/w), more preferably 8-30% (w/w).

The pH of the composition comprising substrate protein may be adjusted and monitored according to methods generally known in the art. The pH of the composition may be adjusted and maintained at from about pH 5 to about pH 10. In one embodiment, the pH of the composition may be adjusted and maintained at from about pH 6.5 to about pH 9. In a preferred embodiment, the pH of the compostion may be adjusted and maintained at about pH 7-8. In another embodiment, the pH of the composition comprising substrate protein is not adjusted.

Thermostable Endopeptidase

In the methods of the present invention, a thermostable endopeptidase is added to the composition comprising substrate protein.

Endopeptidase activity may be determined by using one of the assays of the Examples.

A thermostable endopeptidase in the context of the present invention may be defined as an endopeptidase, which after incubation for 15 minutes at 80° C. and a pH where the endopeptidase exhibits at least 40% of its maximum activity has a residual activity of at least 80% relative to its activity after incubation at 37° C.

A thermostable endopeptidase in the context of the present invention may be defined as an endopeptidase, which after incubation for 15 minutes at 80° C. and pH 9 has a residual activity of at least 80% relative to its activity after incubation at 37° C.

The residual activity may be determined using the Residual Activity Measurement assay as described in the Examples.

Preferably, the thermostable endopeptidase is an endopeptidase, which after incubation for 15 minutes at 90° C.

and a pH where the endopeptidase exhibits at least 40% of its maximum activity has a residual activity of at least 80% relative to its activity after incubation at 37° C. More preferably, the thermostable endopeptidase is an endopeptidase, which after incubation for 15 minutes at 95° C. and a pH where the endopeptidase exhibits at least 40% of its maximum activity has a residual activity of at least 80% relative to its activity after incubation at 37° C.

The thermostable endopeptidase may be an endopeptidase, which after incubation for 15 minutes at 80° C., preferably 90° C., more preferably 95° C., and pH 9 has a residual activity of at least 80% relative to its activity after incubation at 37° C.

The thermostable endopeptidase may have at least 20%, preferably at least 30%, at least 40%, at least 50%, at least 60%, at least 70% or at least 80%, of the endopeptidase activity of the polypeptide of SEQ ID NO: 3. The skilled person will know how to determine the endopeptidase activity, e.g., by using one of the assays of the Examples.

In a preferred embodiment, the thermostable endopeptidase has at least 20%, preferably at least 30%, at least 40%, at least 50%, at least 60%, at least 70% or at least 80%, of the endopeptidase activity of the polypeptide of SEQ ID NO: 3 after incubation at 80° C. and pH 9 for 15 minutes, where the endopeptidase activity is measured according to the Relative Activity Assay.

In a preferred embodiment, the thermostable endopeptidase is a nonspecific endopeptidase. The skilled person will know if an endopeptidase is a specific endopeptidase, which, e.g., cleaves after Arg or Lys, or if it is a nonspecific endopeptidase. A nonspecific endopeptidase may also be characterized as an endopeptidase having a broad specificity.

A nonspecific endopeptidase may be characterized in that incubation of 0.5% (w/w) BSA with the endopeptidase for 4 hours at a temperature and pH where the endopeptidase exhibits at least 40% of its maximum activity results in a degree of hydrolysis of at least 10%, preferably at least 15%.

In some embodiments, the thermostable endopeptidase has been isolated.

In some embodiments, the thermostable endopeptidase has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. The thermostable endopeptidase may differ by up to 10 amino acids, e.g., 1, 2, 3, 4, 5, 6, 7, 8, 9, or 10, from the mature polypeptide of SEQ ID NO: 2.

In the context of the present invention, the term "mature polypeptide" means a polypeptide in its final form following translation and any post-translational modifications, such as N terminal pro-cessing, C terminal truncation, glycosylation, phosphorylation, etc. In one aspect, the mature polypeptide is amino acids 111 to 523 of SEQ ID NO: 2. It is known in the art that a host cell may produce a mixture of two of more different mature polypeptides (i.e., with a different C terminal and/or N terminal amino acid) expressed by the same polynucleotide. It is also known in the art that different host cells process polypeptides differently, and thus, one host cell expressing a polynucleotide may produce a different mature polypeptide (e.g., having a different C terminal and/or N terminal amino acid) as compared to another host cell expressing the same polynucleotide.

The mature polypeptide of SEQ ID NO: 2 has been experimentally determined as amino acids 111-523 using SDS-PAGE in-gel digest and liquid chromatography and high resolution mass spectrometry. A peptide map has been made covering 68% of the mature sequence including both the N-terminal and the C-terminal.

In the context of the present invention, the term "sequence identity" is a measure of the related-ness between two amino acid sequences or between two nucleotide sequences.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment).

In some embodiments, the thermostable endopeptidase has a sequence identity to the polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. The thermostable endopeptidase may differ by up to 10 amino acids, e.g., 1, 2, 3, 4, 5, 6, 7, 8, 9, or 10, from the polypeptide of SEQ ID NO: 3.

In some embodiments, the thermostable endopeptidase comprises or consists of the amino acid sequence of SEQ ID NO: 3 or an allelic variant thereof.

In some embodiments, the thermostable endopeptidase is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In the context of the present invention, the term "mature polypeptide coding sequence" means a polynucleotide that encodes a mature polypeptide having endopeptidase activity. In one aspect, the mature polypeptide coding sequence is nucleotides 331 to 1569 of SEQ ID NO: 1.

In some embodiments, the thermostable endopeptidase is a variant of the mature polypeptide of SEQ ID NO: 2 comprising a substitution, deletion, and/or insertion at one or more (e.g., several) positions. In some embodiments, the number of amino acid substitutions, deletions and/or insertions introduced into the mature polypeptide of SEQ ID NO: 2 is up to 10, e.g., 1, 2, 3, 4, 5, 6, 7, 8, 9, or 10.

In some embodiments, the thermostable endopeptidase is a variant of the polypeptide of SEQ ID NO: 3 comprising a substitution, deletion, and/or insertion at one or more (e.g., several) positions. In some embodiments, the number of amino acid substitutions, deletions and/or insertions introduced into the polypeptide of SEQ ID NO: 3 is up to 10, e.g., 1, 2, 3, 4, 5, 6, 7, 8, 9, or 10.

In the context of the present invention, the term "variant" means a polypeptide having endopeptidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adja-cent to and immediately following the amino acid occupying a position.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threo-nine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may affect the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for endopeptidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Low-man et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

A thermostable endopeptidase to be used in a method of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The thermostable endopeptidase may be obtained from an organism characterized as a hyperthermophile. The endopeptidase may be obtained from a hyperthermophilic bacterium, e.g., from *Thermotoga, Thermosipho, Fervidobacterium, Aquifex, Calderobacterium, Thermocrinis*, or it may be obtained from archaea, e.g., from *Sulfolobus, Metallosphaera, Acidianus, Stygiolobus, Sulfurococcus, Sulfurisphaera, Thermoproteus, Pyrobaculum, Thermofilum, Thermocladium, Caldivirga, Desulfurococcus, Staphylothermus, Sulfophobococcus, Stetteria, Aeropyrum, Ignicoccus, Thermosphaera, Thermodiscus, Pyrodictium, Hyperthermus, Pyrolobus, Thermococcus, Pyrococcus, Archaeoglobus, Ferroglobus, Methanothermus, Methanococcus, Methanopyrus*.

In some preferred embodiments, the thermostable endopeptidase may be obtained from *Pyrococcus*. In some preferred embodiments, the thermostable endopeptidase may be obtained from *Pyrococcus furiosus*.

Strains of *Pyrococcus* are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The thermostable endopeptidase may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the thermostable endopeptidase may then be obtained by similarly screening a genomic DNA or cDNA library of another microorganism or mixed DNA sample. Once a polynucleotide encoding a thermostable endopeptidase has been detected with the probe(s), the polynucleotide can be isolated or cloned by utilizing techniques that are known to those of ordinary skill in the art (see, e.g., Sambrook et al., 1989, supra).

In some preferred embodiments, the thermostable endopeptidase may be a variant of an endopeptidase obtained from *Pyrococcus*. In some preferred embodiments, the thermostable endopeptidase may be a variant of an endopeptidase obtained from *Pyrococcus furiosus*.

The thermostable endopeptidase may be a variant of an endopeptidase obtained from any organism, such as from an organism characterized as a hyperthermophile, e.g., from one of the hyperthermophilic organisms listed above. Alternatively, the thermostable endopeptidase may be a variant of an endopeptidase obtained from an organism which is not a hyperthermophile, such as a variant having a higher thermostability.

In some embodiment, the endopeptidase is an S8 endopeptidase, e.g., an S8 protease from *Pyrococcus*, preferably from *Pyrococcus furiosus*.

In some embodiments, the thermostable endopeptidase has a sequence identity to the polypeptide of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. The thermostable endopeptidase may differ by up to 10 amino acids, e.g., 1, 2, 3, 4, 5, 6, 7, 8, 9, or 10, from the polypeptide of SEQ ID NO: 4.

In some embodiments, the thermostable endopeptidase comprises or consists of the amino acid sequence of SEQ ID NO: 4 or an allelic variant thereof.

In some embodiments, the thermostable endopeptidase is a variant of the mature polypeptide of SEQ ID NO: 4 comprising a substitution, deletion, and/or insertion at one or more (e.g., several) positions. In some embodiments, the number of amino acid substitutions, deletions and/or insertions introduced into the mature polypeptide of SEQ ID NO: 4 is up to 10, e.g., 1, 2, 3, 4, 5, 6, 7, 8, 9, or 10.

In some preferred embodiments, the thermostable endopeptidase may be obtained from *Nocardiopsis prasina*.

In some embodiments, the thermostable endopeptidase may be a variant of an endopeptidase obtained from *Nocardiopsis*. In some embodiments, the thermostable endopeptidase may be a variant of an endopeptidase obtained from *Nocardiopsis prasina*.

In some embodiments, the thermostable endopeptidase may be a serine protease, e.g., a serine protease from *Nocardiopsis*, preferably from *Nocardiopsis prasina*.

In some embodiments, the thermostable endopeptidase has a sequence identity to the mature polypeptide of SEQ ID NO: 6, e.g., to amino acids 183-368 of SEQ ID NO: 6, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. The thermostable endopeptidase may differ by up to 10 amino acids, e.g., 1, 2, 3, 4, 5, 6, 7, 8, 9, or 10, from the mature polypeptide of SEQ ID NO: 6.

In some embodiments, the thermostable endopeptidase comprises or consists of the amino acid sequence of the mature polypeptide of SEQ ID NO: 6 or an allelic variant thereof.

In some embodiments, the thermostable endopeptidase is a variant of the mature polypeptide of SEQ ID NO: 6 comprising a substitution, deletion, and/or insertion at one or more (e.g., several) positions. In some embodiments, the number of amino acid substitutions, deletions and/or insertions introduced into the mature polypeptide of SEQ ID NO: 6 is up to 10, e.g., 1, 2, 3, 4, 5, 6, 7, 8, 9, or 10.

In some embodiments, the thermostable endopeptidase has a sequence identity to the polypeptide of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. The thermostable endopeptidase may differ by up to 10 amino acids, e.g., 1, 2, 3, 4, 5, 6, 7, 8, 9, or 10, from the polypeptide of SEQ ID NO: 8.

In some embodiments, the thermostable endopeptidase comprises or consists of the amino acid sequence of the polypeptide of SEQ ID NO: 8 or an allelic variant thereof.

In some embodiments, the thermostable endopeptidase is a variant of the polypeptide of SEQ ID NO: 8 comprising a substitution, deletion, and/or insertion at one or more (e.g., several) positions. In some embodiments, the number of amino acid substitutions, deletions and/or insertions introduced into the polypeptide of SEQ ID NO: 8 is up to 10, e.g., 1, 2, 3, 4, 5, 6, 7, 8, 9, or 10.

In some preferred embodiments, the thermostable endopeptidase may be obtained from *Thermobifida*. In some preferred embodiments, the thermostable endopeptidase may be obtained from *Thermobifida fusca*.

In some embodiments, the thermostable endopeptidase may be a variant of an endopeptidase obtained from *Thermobifida*. In some embodiments, the thermostable endopeptidase may be a variant of an endopeptidase obtained from *Thermobifida fusca*.

In some embodiments, the thermostable endopeptidase may be an S1A protease, e.g., an S1A protease from *Thermobifida*, preferably from *Thermobifida fusca*.

The thermostable endopeptidase may be one of the variants of a protease from *Thermoascus aurantiacus* having a higher thermostability which are disclosed in WO 2011/072191.

The amount of thermostable endopeptidase added to the composition comprising substrate protein can and will vary depending upon the source of the substrate protein, the desired degree of hydrolysis, and the duration of the hydrolysis reaction. The amount of thermostable endopeptidase may range from about 1 mg of enzyme protein to about 5000 mg of enzyme protein per kilogram of dry matter. In another embodiment, the amount may range from 10 mg of enzyme protein to about 2000 mg of enzyme protein per kilogram of dry matter. In yet another embodiment, the amount may range from about 50 mg of enzyme protein to about 1000 mg of enzyme protein per kilogram of dry matter.

Hydrolysis of Substrate Protein with Thermostable Endopeptidase

After addition of the thermostable endopeptidase, the composition is incubated for at least 10 minutes at a temperature of at least 75° C. In some preferred embodiments, the composition is incubated for at least 30 minutes, e.g., for at least 1 hour or at least 2 hours. In some preferred embodiments, the composition is incubated for 10 minutes to 20 hours, e.g., for 30 minutes to 10 hours or for 1-8 hours.

In some preferred embodiments, the composition is incubated at a temperature of at least 80° C., e.g., at least 85° C., at least 90° C. or at least 95° C. In some preferred embodiments, the composition is incubated at a temperature of 75-120° C., e.g., 80-115° C., 85-110° C., 90-105° C. or 95-100° C.

Second Hydrolysis with a Protease Preparation Having Aminopeptidase Activity

In some aspects of the present invention, after the first hydrolysis step with the thermostable endopeptidase, a protease preparation having an aminopeptidase activity of at least 200 LAPU/g is added to the composition and a second hydrolysis step is performed by incubating for at least 10 minutes at a temperature which is at least 10° C. lower than the temperature used in the first hydrolysis step.

After the first hydrolysis step, the pH of the composition may be adjusted according to methods generally known in the art. The pH of the composition may be adjusted and maintained during the second hydrolysis step at from about pH 5 to about pH 10. In one embodiment, the pH of the composition may be adjusted and maintained at from about pH 7 to about pH 9, e.g., at about pH 8. In a preferred embodiment, the pH of the composition is not adjusted before the second hydrolysis step.

The protease preparation may have an aminopeptidase activity of at least 300 LAPU/g, preferably at least 500 LAPU/g, more preferably at least 1000 LAPU/g. One LAPU (leucine amino peptidase) is defined as the amount that hydrolyzes 1 mmol L-leucine-p-nitroanilide per minute at 37° C., pH 8.0. The absorption increase of the product p-nitroaniline is measured at 405 nm and is proportional to the enzyme activity.

The protease preparation may have an aminopeptidase activity of 200-5000 LAPU/g, preferably 500-2000 LAPU/g.

Preferably, the protease preparation is added in a total amount of at least 1 LAPU/g dry matter, preferably at least 5 LAPU/g dry matter, more preferably at least 8 LAPU/g dry matter.

Preferably, the protease preparation has a carboxypeptidase activity of at least 5 CPDU/g, preferably at least 10 CPDU/g, more preferably at least 20 CPDU/g. One CPDU (carboxypeptidase unit) is defined as the amount of enzyme that hydrolyzes 1 μmole N-(3-[2-furyl]acryloyl)-Ala-Lys per minute at 37° C., pH 5.8. The absorption decrease is measured at 340 nm and is proportional to the enzyme activity.

The protease preparation may have a carboxypeptidase activity of 5-2000 CPDU/g, preferably 10-1000 CPDU/g.

Preferably, the protease preparation is added in a total amount of at least 0.02 CPDU/g dry matter, preferably at least 0.1 CPDU/kg dry matter, more preferably at least 0.15 CPDU/kg dry matter.

In a preferred embodiment, the protease preparation comprises at least five proteolytic components each having an approximate molecular weight, respectively, selected from 23 kD, 27 kD, 31 kD, 32 kD, 35 kD, 38 kD, 42 kD, 47 kD, 53 kD, and 100 kD. In another preferred embodiment, the protease preparation comprises at least five proteolytic components having the approximate molecular weights 23 kD, 31 kD, 35 kD, 38 kD and 53 kD, respectively.

Preferably the protease preparation is dervied from a fungus, more preferably a filamentous fungus.

In a preferred embodiment, the protease preparation is dervied from *Aspergillus*, preferably from *Aspergillus oryzae*.

The protease preparation may be the protease preparation derived from *Aspergillus oryzae* which is described in WO94/25580.

The protease preparation may be the protease preparation derived from *Aspergillus oryzae* supplied from Novozymes A/S under the tradename Flavourzyme®. The protease preparation may be the protease preparation Protease A "Amano" 2 SD from a strain of *Aspergillus oryzae* (Amano).

After the first hydrolysis step, the temperature of the compostion is adjusted to a temperature which is at least 10° C. lower than the temperature used in the first hydrolysis step. The temperature may be adjusted before, during or after the addition of the protease preparation. Preferably, the temperature is adjusted before addition of the protease preparation.

After addition of the protease preparation, the composition is incubated for at least 10 minutes at such temperature. In some preferred embodiments, the composition is incubated for at least 30 minutes, preferably for at least 1 hour, e.g., for at least 2 hours or for at least 4 hours after addition of the protease preparation. In some preferred embodiments, the composition is incubated for 10 minutes to 72 hours, e.g., for 1-48 hours or for 2-24 hours after addition of the protease preparation.

In some preferred embodiments, the composition is incubated at a temperature of 30-65° C., e.g., 35-60° C., 40-60° C. or 45-55° C.

An enzyme capable of converting Gln to Glu may be added at the same time as or after the addition of the protease preparation. It may be, e.g., a glutaminase or a gamma-glutamyl-trans-peptidase.

Protein Hydrolysate Obtained

The degree of hydrolysis of a protein hydrolysate obtained by a method of the present invention can and will vary depending upon the source of the substrate protein, the protease(s) used, and the degree of completion of the hydrolysis reaction.

The degree of hydrolysis (DH) refers to the percentage of peptide bonds cleaved versus the starting number of peptide bonds. For example, if a starting protein containing five hundred peptide bonds is hydrolyzed until fifty of the peptide bonds are cleaved, then the DH of the resulting hydrolysate is 10%. The degree of hydrolysis may be determined using the trinitrobenzene sulfonic (TNBS) colorimetric method or the orthophthaldialdehyde (OPA) method, as detailed in the examples. The higher the degree of hydrolysis, the greater the extent of protein hydrolysis.

If the substrate protein is soy protein, the degree of hydrolysis of a protein hydrolysate obtained by a method of the present invention may be at least 10%, more preferably at least 15%, at least 20% or at least 30%. In some embodiments, the degree of hydrolysis of the protein hydrolysate is 10-100%, preferably 15-80% or 20-60%. Preferably, the degree of hydrolysis is determined using the OPA method.

The solubility of a protein hydrolysate obtained by a method of the present invention can and will vary depending upon the source of the source of the substrate protein, the protease(s) used, and the pH of the composition. The solubility is a measure of the solubility of the solids (i.e., polypeptide fragments) in the protein hydrolysate. The amount of soluble solids may be estimated by measuring the amount of solids in solution before and after centrifugation (e.g., about 500-1000×g for about 5-10 min). Alternatively, the amount of soluble solids may be determined by estimating the amount of protein in the composition before and after centrifugation using a technique well known in the art, such as, e.g., a bicinchoninic acid (BCA) protein assay or by measuring the protein content of the supernatant (obtained by centrifugation at 1200 for 5 min) relative to the protein content of the whole sample as described in the Examples.

Preferably, the solubility of a protein hydrolysate obtained by a method of the present invention is at least 60%, more preferably at least 65% or at least 70%. In some embodiments, the solubility of the protein hydrolysate is 60-100%, preferably 65-100% or 70-100%.

EXAMPLES

The experimental Thermostable protease (PFus) used in the Examples is the endopeptidase of SEQ ID NO: 3.

Example 1

Hydrolysis of Soy Bean Meal (SBM) with Experimental Thermostable Protease (PFus) in Comparison with the State of the Art Enzyme, Alcalase 2.4 L A hydrolysis assay has been performed in 12% soy solution. The solution was prepared by suspending 42 g soy bean meal in 308 g demineralized water (Milli Q water). pH was adjusted to pH 8 by 4N NaOH. 40 g SBM suspensions were heated to 70° C. and 95° C., respectively; 0.25% Alcase 2.4 L was added to the 70° C. SBM suspension and 50 or 100 mg ep/kg SBM of PFus was added to the 95° C. SBM suspension. A control with no enzyme added has been included for both temperatures. The samples were incubated for 30, 60 and 120 min with stirring. Small amounts, i.e. 1.5 ml of each of the samples were withdrawn after 30, 60 and 120 min and the enzymatic hydrolysis was stopped immediately for PFus by placing the samples in an ice bath and for the Alcalase samples by heating the samples at 95° C. for 15 min. Samples were in general frozen until analysis and handled on ice when in use. % DH was measured in duplicate on the suspension by OPA and solubility was measured in duplicate by the BCA method.

The degree of hydrolysis (% DH) of each of the hydrolysates was determined by using the o-phtaldialdehyde (OPA) assay. For this, each hydrolysate (and non-hydrolyzed starting material) was diluted to 2.5% dry matter and afterwards diluted 1:20. 20 µl aliquot of each sample/standard was transferred to microtiter plates (MTP) and 200 µl OPA reagent was added (OPA reagent: The following reagents are weighed in 100 ml measuring flask and dissolved in milli Q water, milli Q water added up to 100 ml: 0.504 g Sodium bicarbonate, 0.4293 g Sodium carbonate decahydrate, 100 mg Sodium dodecyl sulphate (SDS), 88 g di-thiotritol (DTT), 80 mg o-phthaldehyde (OPA) dissolved in 2 ml 96% ethanol). The absorbance was measured at 340 nm. A standard curve with L-serine (0-0.5 mg/ml) was also included. The degree of of hydrolysis was calculated as related to the serine standard.

Solubility analysis: The ratio of soluble solids of each hydrolysates was determined by measuring the soluble protein using bicinchoninic acid (BCA) based protein assay (e.g Micro BCA Protein Assay Kit; Sigma BCA1). BCA was measured on the very sample and on supernatants. Full samples are diluted to 2.5% dry matter and 1.5 ml of the 2.5% dry matter samples are centrifuged 10 min at 500 G. All samples are diluted 1:20. BSA (bovine serum albumin) standard dilution (0-1.0 mg/ml) was included in each MTP. 20 µL of each sample and standard are transferred to MTP (Micro Titer Plates). 160 µL BCA reagent (8 ml Bicinchoninic Acid+Copper sulphate 4% w/v solution) is added. MTP plates are incubated 30 min at 37° C. and the absorbance at 582 nm is measured. The absorbance at 582 nm is directly proportional to the protein concentration and the solubility is then calculated as the protein concentration in the supernatant relative to the very sample.

The results appear from the table below. It is clearly seen that on all aspects % DH and solubility of the samples treated with the thermostable protease PFus are superior to Alcalase.

TABLE 1

Comparison of PFus and Alcalase 2.4 L on the two parameters % DH and Solubility

|  | Solubility % | DH % |
|---|---|---|
| Process ref 70° C., 120 min | 67 | 6.5 |
| 0.25 % Alcalase, 30 min | 80 | 9.7 |
| 0.25 % Alcalase, 60 min | 80 | 10.6 |
| 0.25 % Alcalase, 120 min | 73 | 12.4 |
| Process ref 95° C., 120 min | 71 | 6 |
| PFus 50 mg/kg, 30 min | 86 | 10 |
| PFus 50 mg/kg, 60 min | 82 | 12.2 |
| PFus 50 mg/kg, 120 min | 89 | 13.4 |
| PFus 100 mg/kg, 30 min | 88 | 10.7 |
| PFus 100 mg/kg, 60 min | 90 | 12.1 |
| PFus 100 mg/kg, 120 min | 87 | 14.2 |

Example 2

Hydrolysis of Soy Bean Meal (SBM) with a Combination of Experimental Thermostable Protease (PFus) and Flavourzyme 1000 L in Comparison with the State of the Art Enzyme, Alcalase 2.4 L and Flavourzyme 1000 L.

A hydrolysis assay has been performed in a two-step hydrolysis procedure. 12% soy solution was prepared by suspending 42 g soy bean meal in 308 g demineralized water (Milli Q water). pH was adjusted to pH 8 by 4N NaOH. 30 g SBM suspensions were heated to 70° C. and 95° C., respectively, 0.25% Alcase 2.4 L was added to the 70° C. SBM suspension and 100 mg ep/kg SBM of PFus was added to the 95° C. SBM suspension. A control with no enzyme added has been included. The samples were incubated for 120 min with stirring. All samples were then adjusted to 50° C. and 0.5, 1.5 and 3.0% Flavourzyme 1000 L (having at least 1000 LAPU/g and at least 20 CPDU/g), respectively, was added. The samples were left for 20 h at 50° C. Small amounts, i.e. 1.5 ml of each of the samples were withdrawn after 2, 4 and 20 hours after start and the enzymatic hydrolysis was stopped immediately either by placing the samples in an ice bath or by heating the samples at 100° C. for 10 min. Samples were in general frozen until analysis and handled on ice when in use. % DH was measured in duplicate on the suspension by OPA and solubility was measured in duplicate by the BCA method. The results appear from the table below.

It is clearly seen that on the analyzed parameters, % DH and solubility for the thermostable enzyme either alone or in combination with Flavourzyme is superior to Alcalase.

TABLE 2

Comparison of PFus and Alcalase 2.4 L in combination with Flavourzyme 1000 L on the two parameters % DH and Solubility

|  | Solubility % | DH % |
|---|---|---|
| PFus 100 mg/kg, 2 h | 88 | 10.1 |
| PFus + 0.5% Flavourzyme, 4 h | 80 | 16.9 |
| PFus + 1.5% Flavourzyme, 4 h | 79 | 23.8 |
| PFus + 3% Flavourzyme, 4 h | 86 | 29.2 |
| 0.25% Alc, 2 h | 71 | 9.7 |
| Alc + 0.5% Flavourzyme, 4 h | 57 | 16.3 |
| Alc + 1.5% Flavourzyme, 4 h | 64 | 19.7 |

TABLE 2-continued

Comparison of PFus and Alcalase 2.4 L in combination with
Flavourzyme 1000 L on the two parameters % DH and Solubility

|  | Solubility % | DH % |
|---|---|---|
| Alc + 3% Flavourzyme, 4 h | 65 | 22.8 |
| PFus + 0.5% Flavourzyme, 20 h | 96 | 24.6 |
| PFus + 1.5% Flavourzyme, 20 h | 85 | 35.2 |
| PFus + 3% Flavourzyme, 20 h | 67 | 40 |
| Alc + 0.5% Flavourzyme, 20 h | 56 | 23.9 |
| Alc + 1.5% Flavourzyme, 20 h | 54 | 31.5 |
| Alc + 3% Flavourzyme, 20 h | 61 | 39.6 |

Example 3

Performance of PFus in Comparison with Alcalase 2.4 L for Wheat Gluten Hydrolysis 15% wheat gluten, Tereos Syrah was prepared by suspending 75 g gluten in 425 g Milli Q water, pH is adjusted to pH 8.0 with 4N NaOH. For each test sample 100 g suspension was heated to 70° C. and 95° C., respectively; 0.25% Alcase 2.4 L was added to the 70° C. gluten suspension and 100 mg ep/kg gluten of PFus was added to the 95° C. gluten suspension. A control with no enzyme added has been included. The samples were incubated for 60, 120 and 240 min with stirring. After 240 min the samples with PFus and Alcalase, respectively, were split in two 50 g samples. All samples were then adjusted to 50° C. and 1.0 or 3.0% w/w Flavourzyme 1000 L was added to each sample. The samples with +3% Flavourzyme were left for 4 h at 50° C. and the samples with +1% Flavourzyme were left for 16 h at 50° C. Small amounts, i.e. 1.5 ml of each of the samples were withdrawn after each step 60, 120, 240 min, 4 h, 16 h and the enzymatic hydrolysis was stopped immediately either by placing the samples in an ice bath or by heating the samples at 100*C for 10 min. Samples were in general frozen until analysis and handled on ice when in use. % DH was measured in duplicate on the suspension by OPA and solubility was measured in duplicate by the BCA method. The results appear from the table below. Solubility for the thermostable enzyme either alone or in combination with Flavourzyme is superior to Alcalase.

TABLE 3

Wheat gluten hydrolysis: Comparison of PFus and
Alcalase 2.4 L alone and in combination with Flavourzyme
1000 L on the two parameters % DH and Solubility

| samp. No | | Solubility % | DH % |
|---|---|---|---|
| 19 | Untreated Gluten | 66 | 0.1 |
| 1 | Process ref 70° C. - 60 min | 75 | 0.3 |
| 2 | Alcalase -60 min | 70 | 4.1 |
| 3 | Process ref 95° C. -60 min | 59 | 0.4 |
| 4 | PFus -60 min | 91 | 2.1 |
| 5 | Process ref 70° C. - 120 min | 79 | 0.3 |
| 6 | Alcalase - 120 min | 77 | 4.4 |
| 7 | Process ref 95° C. - 120 min | 74 | 0.4 |
| 8 | PFus - 120 min | 97 | 2.9 |
| 9 | Process ref 70° C. - 240 min | 82 | 0.3 |
| 10 | Alcalase - 240 min | 77 | 5 |
| 11 | Process ref 95° C. - 240 min | 70 | 0.7 |
| 12 | PFus - 240 min | 110 | 2.6 |
| 13 | Process ref 70° C. - 240 min + 17 h | 47 | 0.2 |
| 15 | Process ref 95° C. - 240 min + 17 h | 45 | 1 |
| 14 | Alcalase - 240 + 1 % FZ | 57 | 25.3 |

TABLE 3-continued

Wheat gluten hydrolysis: Comparison of PFus and
Alcalase 2.4 L alone and in combination with Flavourzyme
1000 L on the two parameters % DH and Solubility

| samp. No | | Solubility % | DH % |
|---|---|---|---|
| 16 | PFus - 240 + 1 % FZ | 82 | 21.7 |
| 17 | Alcalase- 4 h + 3 % FZ 4 h | 66 | 17.5 |
| 18 | PFus - 4 h + 3 % FZ 4 h | 77 | 15.3 |

Example 4

Characterization of the Experimental Thermostable Protease (PFus)

pH Activity Profile

Assay Principle:

A kinetic Suc-AAPF-pNA assay was used for recording the pH-activity profile. The increase in $OD_{405}$ was monitored over time as a measure of the protease activity.

Assay Buffers:

100 mM succinic acid, 100 mM HEPES, 100 mM CHES, 100 mM CABS, 1 mM $CaCl_2$), 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

Assay Substrate Solution:

50 mg Suc-AAPF-pNA (Bachem L-1400) dissolved in 1.0 mL DMSO and further diluted 45× with 0.01% Triton X-100.

Assay Conditions:

The purified protease stock solution was diluted using 0.01% Triton X-100 in order to ensure an adequate response at the selected assay conditions. 20 μL protease solution was mixed with 100 μL assay buffer in a microtiterplate. The assay was started by adding 100 μL pNA substrate solution and the increase in $OD_{405}$ was monitored over time.

| pH | Relative Activity (%) |
|---|---|
| 2 | 0.2 |
| 3 | 0.3 |
| 4 | 4.7 |
| 5 | 31.6 |
| 6 | 69.7 |
| 7 | 82.4 |
| 8 | 82.7 |
| 9 | 84.5 |
| 10 | 90.3 |
| 11 | 100.0 | pH Stability as Evaluated by Residual Activity Measurements

Assay Principle:

A kinetic Suc-AAPF-pNA assay was used for obtaining the pH stability profile at 37° C. The increase in $OD_{405}$ was monitored over time as a measure of the protease activity.

Incubation Buffers:

100 mM succinic acid, 100 mM HEPES, 100 mM CHES, 100 mM CABS, 1 mM $CaCl_2$), 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

Assay Buffer:

0.5 M Tris/HCl, 2 mM CaCl$_2$), pH 9.0.

Assay Substrate Solution:

50 mg Suc-AAPF-pNA (Bachem L-1400) dissolved in 1.0 mL DMSO and further diluted 45× with 0.01% Triton X-100.

Assay Conditions:

The purified protease stock solution was diluted using incubation buffer at selected pH's in order to ensure the correct incubation pH and a protease concentration of approx. 0.1 mg/mL. This was followed by incubation at 37° C. for 2 hrs. Then the protease samples were transferred to the same pH (pH 9), before assay for residual activity, by dilution in assay buffer to ensure an adequate response in the assay for residual activity. The residual activity in the samples was measured by mixing 20 µL protease solution with 100 µL assay buffer in a microtiterplate. The assay was started by adding 100 µL pNA substrate. The increase in OD$_{405}$ was monitored over time. The reference sample was kept at 5° C. throughout the incubation step. The data listed in the table below are the residual activities relative to the activity recorded for the sample incubated at 5° C.

| pH | Residual Activity (%) |
|---|---|
| 2 | 1.5 |
| 3 | 1.0 |
| 4 | 96.3 |
| 5 | 95.7 |
| 6 | 101.5 |
| 7 | 102.1 |
| 8 | 100.8 |
| 9 | 99.1 |
| 10 | 98.7 |
| 11 | 104.1 |
| 5° C. | 100.0 |

Temperature Stability as Evaluated by Residual Activity Measurements

Assay Principle:

A kinetic Suc-AAPF-pNA assay was used for obtaining the temperature-stability profile at pH 9. The increase in OD$_{405}$ was monitored over time as a measure of the protease activity.

Assay Buffer:

100 mM succinic acid, 100 mM HEPES, 100 mM CHES, 100 mM CABS, 1 mM CaCl$_2$), 150 mM KCl, 0.01% Triton X-100, pH 9.0.

Assay Substrate Solution:

50 mg Suc-AAPF-pNA (Bachem L-1400) dissolved in 1.0 mL DMSO and further diluted 45× with 0.01% Triton X-100.

Assay Conditions:

The purified protease stock solution was diluted using incubation buffer in order to ensure the correct assay pH and a protease concentration of approx. 0.1 mg/mL. This was followed by incubation at selected temperatures for 15 min. After incubation the residual activity in the samples was measured by mixing 20 µL protease solution with 100 µL assay buffer in a microtiterplate. The assay was started by adding 100 µL pNA substrate. The increase in OD$_{405}$ was monitored over time. The data listed in the table below are the residual activities relative to the activities recorded for the incubations at 37° C.

| Temperature (° C.) | Residual Activity (%) |
|---|---|
| 37 | 99.0 |
| 50 | 99.8 |
| 60 | 100.0 |
| 70 | 99.9 |
| 80 | 99.5 |
| 90 | 97.9 |
| 99 | 84.6 |

Temperature-Activity Profile

Assay Principle:

An endpoint Suc-AAPF-pNA assay was used for obtaining the temperature-activity profile at pH 9. OD$_{405}$ was recorded as a measure of protease activity.

Assay Buffer:

100 mM succinic acid, 100 mM HEPES, 100 mM CHES, 100 mM CABS, 1 mM CaCl$_2$, 150 mM KCl, 0.01% Triton X-100, pH 9.0.

Assay Substrate Solution:

50 mg Suc-AAPF-pNA (Bachem L-1400) dissolved in 1.0 mL DMSO and further diluted 50× with the assay buffer.

Assay Conditions:

The purified protease stock solution was diluted using 0.01% Triton X-100 in order to ensure an adequate response at the selected assay conditions. 200 µL of assay substrate solution were pipetted in an Eppendorf tube and placed on ice. 20 µL of the diluted protease solution was added and the assay started by transferring the Eppendorf tube to an Eppendorf thermomixer, which was set to the assay temperature. The tube was incubated for 15 minutes at the highest shaking rate (1400 rpm). The incubation was stopped by transferring the tube to the ice bath and adding 600 µL 500 mM succinic acid, pH 3.5. 200 µL supernatant was transferred to a microtiter plate and OD$_{405}$ read as a measure of peptidase activity. A buffer blind was included in the assay (instead of enzyme).

| Temperature (° C.) | Relative Activity (%) |
|---|---|
| 15 | 5.9 |
| 25 | 7.4 |
| 37 | 13.6 |
| 50 | 26.4 |
| 60 | 40.4 |
| 70 | 53.1 |
| 80 | 81.3 |
| 90 | 93.5 |
| 99 | 100.0 |

Example 5

Endo-Protease Activity Assay

Assay Principle:

An endpoint-assay using the Protazyme AK substrate (AZCL-casein) or Protazyme OL substrate (AZCL-collagen), both from Megazyme. OD$_{590}$ is recorded after terminating the reaction. The increase in absorbance reflects solubilized, dye-coupled casein/collagen fragments and is a measure of the protease endo-activity. Protazyme OL is particularly suited for proteases with acidic pH optima.

Assay Buffer:

Selected to fit the requirements of the endo-protease to be tested (e.g. inclusion of known required cofactors). A broad, cocktail buffer serving many needs could be: 100 mM succinic acid, 100 mM HEPES, 100 mM CHES, 100 mM CABS, 1 mM $CaCl_2$), 150 mM KCl, 0.01% Triton X-100 adjusted to pH-values 2.0, 2.5, 3.0, 3.5, 4.0, 4.5, 5.0, 5.5, 6.0, 7.0, 8.0, 9.0, 10.0, and 11.0 with HCl or NaOH.

Assay Substrate Suspension:

A Protazyme AK or Protazyme OL tablet (from Megazyme) was suspended in 2.0 mL 0.01% Triton X-100 by gentle stirring.

Assay Conditions:

500 µL of the assay substrate suspension and 500 µL assay buffer were mixed in an Eppendorf tube and placed on ice. 20 µL protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice-cold centrifuge for a few minutes and 200 µL supernatant was transferred to a microtiter plate. $OD_{590}$ was read as a measure of protease activity. A buffer blind was included in the assay (instead of enzyme).

Example 6

Hydrolysis of Soy Bean Meal (SBM) with Either of Experimental Thermostable Protease from *Thermobifida fusca* (*T. fusca* Protease), Thermostable Serine Protease from *Nocardiopsis prasina* (*Nocardiopsis* protease) or state of the art enzyme Alcalase 2.4 L each combined with Flavourzyme 1000 L The *Nocardiopsis* protease has the amino acid sequence of SEQ ID NO: 4.

The wild-type DNA and amino acid sequence of the *T. fusca* protease are shown as SEQ ID NOs: 5 and 6. The protease has been expressed in *Bacillus subtilis* with a suitable signal sequence replacing the native one and with an HQHQHQH-tag in the C-terminal. The amino acid sequence of the expression construct is shown as SEQ ID NO: 7. The N-terminal has been determined as AAIIGGN (amino acids 183-189 of SEQ ID NO: 6 and 179-185 of SEQ ID NO: 7) using Edman degradation. SEQ ID NO: 8 shows the mature amino acid sequence of the T. *fusca* protease based hereon.

Both the *Nocardiopsis* protease and the T. *fusca* protease have a temperature optimum at or above 80° C.

A hydrolysis assay has been performed in a two-step hydrolysis procedure. 12% soy solution was prepared by suspending 12 g soy bean meal in 88 g demineralized water (Milli Q water). The solution was stirred for 30 min. before pH was adjusted to 8.0 with 4 N NaOH.

For each treatment, 5 g substrate solution was weighed out in 5 ml Eppendorf tubes and heated in an Eppendorf thermomixer, mixing speed=1000 rpm. Proteases were added at room temp. immediately before heating-up to the optimum temperature of the 3 enzymes: Alcalase at 70° C., *Nocardiopsis* protease at 80° C. and *T. fusca* protease at 80° C. The times to reach the optimum temperature range from 10-30 min. Alcalase 2.4 L was added at a dosage of 5.7 AU/kg protein, *T. fusca* protease at 200 mg/kg and *Nocardiopsis* protease at 100 mg/kg After 4 hours 1.5 ml samples are taken out and placed on ice. The temperature of the remaining sample materials were decreased to 50° C. and Flavourzyme 1000 L was added at 1.5%. After 16 hours the samples were placed on ice. All samples (4 hours and 20 hours) were stored in a freezer until analysis was carried out. All samples were analysed for % DH as described in example 1 and % solubility as described below. % solubility was analysed by measuring the protein content of the supernatant (obtained by centrifugation at 1200 for 5 min) relative to the protein content of the whole sample. The protein content of both the whole sample and the supernatant were analysed by a LECO FP628. LECO analysis is based on detection of the nitrogen content by combustion analysis. The nitrogen convertion factor applied is 6.25.

TABLE 4

Comparison of Thermostable *T. fusca* protease, *Nocardiopsis* protease and Alcalase 2.4 L in combination with Flavourzyme 1000 L on the two parameters % DH and Solubility

| | Solubility % | | % DH | |
|---|---|---|---|---|
| | 4 h | 4 + 16 h | 4 h | 4 + 16 h |
| Alcalase 2.4 L 70° C. | 84 +/− 0.1 | | 9.8 +/− 0.3 | |
| *Nocardiopsis* prot 80° C. | 89 +/− 0.05 | | 9.8 +/− 0.14 | |
| *T. fusca* prot 80° C. | 90 +/− 0.03 | | 11.5 +/− 0.8 | |
| Alcalase 2.4 L 70° C. + Flavourzyme 1000 L | | 55 +/− 0.2 | | 29.5 +/− 0.8 |
| *Nocardiopsis* prot 80° C. + Flavourzyme 1000 L | | 67 +/− 0.1 | | 32.6 +/− 0.0 |
| *T. fusca* prot 80° C. + Flavourzyme 1000 L | | 78 +/− 0.5 | | 31.3 +/− 0.5 |

The solubility of the soy samples for the thermostable enzymes either alone or in combination with Flavourzyme were observed as superior to Alcalase. The % DH is also either the same or higher for the thermostable enzymes compared to Alcalase.

---

The invention claimed is:

1. A method for producing a protein hydrolysate, comprising:
   a) adding to a composition comprising a substrate protein a thermostable endopeptidase;
   b) performing a first hydrolysis step by incubating the composition of step a) for at least 10 minutes at a temperature of at least 75° C.;
   c) adding to the composition of step b) a protease preparation having an aminopeptidase activity of at least 200 LAPU/g; and
   d) performing a second hydrolysis step by incubating the composition of step c) for at least 10 minutes at a temperature which is at least 10° C. lower than the temperature used in step b).

2. The method of claim 1, wherein the thermostable endopeptidase is a nonspecific endopeptidase.

3. The method of claim 2, wherein the nonspecific endopeptidase is characterized in that incubation of 0.5% (w/w) BSA with the endopeptidase for 4 hours at a temperature and pH where the endopeptidase exhibits at least 40% of its maximum activity results in a degree of hydrolysis of at least 10%.

4. The method of claim 1, wherein the thermostable endopeptidase is an endopeptidase, which after incubation for 15 minutes at 80° C. and pH 9 has a residual activity of at least 80% relative to its activity after incubation at 37° C.

5. The method of claim 1, wherein the thermostable endopeptidase (i) has at least 60% sequence identity to the polypeptide of SEQ ID NO: 3, (ii) is encoded by a polynucleotide having at least 60% sequence identity to the mature polypeptide coding sequence of SEQ ID NO: 1, or (iii) is a variant of the polypeptide of SEQ ID NO: 3 comprising a substitution, deletion, and/or insertion at one or more positions.

6. The method of claim 1, wherein the thermostable endopeptidase (i) has at least 60% sequence identity to the polypeptide of SEQ ID NO: 8, (ii) is encoded by a polynucleotide having at least 60% sequence identity to the mature polypeptide coding sequence of SEQ ID NO: 5, or (iii) is a variant of the polypeptide of SEQ ID NO: 8 comprising a substitution, deletion, and/or insertion at one or more positions.

7. The method of claim 1, wherein the thermostable endopeptidase (i) has at least 60% sequence identity to the polypeptide of SEQ ID NO: 4, or (ii) is a variant of the polypeptide of SEQ ID NO: 4 comprising a substitution, deletion, and/or insertion at one or more positions.

8. The method of claim 1, wherein the protease preparation added in step c) is a protease preparation from *Aspergillus*.

9. The method of claim 1, where in step d) the composition is incubated at a temperature of 30-65° C.

10. The method of claim 1, wherein an enzyme capable of converting Gln to Glu is added at the same time or after step c).

11. The method of claim 1, wherein the protein hydrolysate obtained in step d) has a degree of hydrolysis of at least 10%.

12. The method of claim 1, wherein the substrate protein is selected from soy protein, wheat gluten protein or whey protein.

13. The method of claim 1, wherein the composition comprising the substrate protein has a dry matter content of at least 1% (w/w).

14. The method of claim 1, wherein the first hydrolysis step is performed at a temperature of 75-120° C. and the second hydrolysis step is performed at a temperature of 30-65° C.

15. The method of claim 1, wherein the first hydrolysis step is performed at a temperature of 80-115° C. and the second hydrolysis step is performed at a temperature of 35-60° C.

16. The method of claim 1, wherein the first hydrolysis step is performed at a temperature of 85-110° C. and the second hydrolysis step is performed at a temperature of 40-60° C.

17. The method of claim 1, wherein the first hydrolysis step is performed at a temperature of 90-105° C. and the second hydrolysis step is performed at a temperature of 45-55° C.

18. The method of claim 1, wherein the protein hydrolysate obtained by the method has a solubility of 60-100%.

19. The method of claim 1, wherein the protein hydrolysate obtained by the method has a solubility of 65-100%.

20. The method of claim 1, wherein the protein hydrolysate obtained by the method has a solubility of 70-100%.

* * * * *